(12) United States Patent
Burke et al.

(10) Patent No.: US 8,904,877 B2
(45) Date of Patent: Dec. 9, 2014

(54) MEANS TO TRACK THE CUMULATIVE COMPRESSIONS IMPARTED TO A SHOE

(71) Applicant: ParaWare LLC, Hamilton, MA (US)

(72) Inventors: Aaron Burke, Hamilton, MA (US);
Daniel Jannsen, Hamilton, MA (US);
Derk Smid, Georgetown, MA (US);
Andrew Hills, Somerville, MA (US)

(73) Assignee: ParaWare LLC, Hamilton, MA (US)

( * ) Notice: Subject to any disclaimer, the term of this patent is extended or adjusted under 35 U.S.C. 154(b) by 253 days.

(21) Appl. No.: 13/692,248

(22) Filed: Dec. 3, 2012

(65) Prior Publication Data

US 2013/0139605 A1 Jun. 6, 2013

Related U.S. Application Data

(60) Provisional application No. 61/567,316, filed on Dec. 6, 2011.

(51) Int. Cl.
*G01B 7/16* (2006.01)
*G01N 3/34* (2006.01)
*A43B 3/00* (2006.01)
*G01N 3/56* (2006.01)

(52) U.S. Cl.
CPC .............. *G01N 3/342* (2013.01); *A43B 3/0005* (2013.01); *G01N 3/56* (2013.01); *G01N 2203/0244* (2013.01)
USPC ................................................ 73/768; 73/818

(58) Field of Classification Search
USPC ..................... 73/768, 774, 818, 821
See application file for complete search history.

(56) References Cited

U.S. PATENT DOCUMENTS

| | | | |
|---|---|---|---|
| 5,471,405 A | 11/1995 | Marsh | |
| 5,640,786 A | 6/1997 | Buyayez | |
| 5,894,682 A | 4/1999 | Broz | |
| 6,186,000 B1 * | 2/2001 | Kaneko et al. | 73/172 |
| 6,578,291 B2 | 6/2003 | Hirsch et al. | |
| 7,623,987 B2 * | 11/2009 | Vock et al. | 702/182 |
| 7,735,351 B2 * | 6/2010 | Profit et al. | 73/11.04 |
| 7,911,339 B2 | 3/2011 | Vock et al. | |
| 8,749,380 B2 * | 6/2014 | Vock et al. | 340/540 |
| 2007/0033838 A1 | 2/2007 | Luce et al. | |

* cited by examiner

*Primary Examiner* — Max Noori
(74) *Attorney, Agent, or Firm* — Nields, Lemack & Frame, LLC (57) ABSTRACT

A device, inserted in a running shoe is used to track the accumulation of destructive compression cycles within the shoe and to indicate this information to the user through a series of integrated indicators. The device has an advantage of being able to be placed in any shoe without compromising the construction or performance of the shoe. An additional advantage of the invention is the improved accuracy of the information by improving both the stability and longevity of the sensor system and the ability to distinguish destructive, partially destructive and nondestructive compressions. Another advantage of the invention is the reduction of the cost of construction while achieving a lifetime in excess of the shoe. Yet another advantage of the invention is the user interface, which is contained completely within the device allowing the user to view the information within the shoe.

14 Claims, 13 Drawing Sheets

| WEIGHT OF RUNNER (LBS) | | | | | | | | |
|---|---|---|---|---|---|---|---|---|
| HEEL STRIKE | 100 | 125 | 150 | 175 | 200 | 250 | 300 | |
| STANDING (0.5x) | 50 | 63 | 75 | 88 | 100 | 125 | 150 | |
| WALKING (1.3x) | 130 | 163 | 195 | 228 | 260 | 325 | 390 | |
| RUNNING (2.5x) | 250 | 313 | 375 | 438 | 500 | 625 | 750 | |

MEANS TO TRACK THE CUMULATIVE COMPRESSIONS IMPARTED TO A SHOE

This application claims priority of U.S. Provisional Patent Application Ser. No. 61/567,316, filed Dec. 6, 2011, the disclosure of which is incorporated herein by reference in its entirety.

BACKGROUND OF THE INVENTION

The present invention relates generally to a shoe having an ability to track the cumulative destructive compressions imparted to a shoe by its user and the ability to indicate that information to the user. More specifically, the present invention relates to an attachment of the shoe that measures the destructive compressions of the shoe, accumulates those compressions and displays the accumulation to the user.

Athletes must replace their shoes as the midsole foam wears due to the cumulative destructive compressions that occur from use. Delaying the replacement of the shoe will lead to injuries caused by the lower extremities absorbing more of the impact. In addition, changes in the characteristics of the midsole foam, such as shape and compression resistance, affects the users ability to control their biomechanical motion during their stance to foot swing phase, also known as the gait of the user, causing inefficiency and injury. Because the construction of the midsole includes microporous foam, detection of this cumulative destruction cannot be determined by a simple external examination. As with other microscopic failure modes, examining a device in a static condition does not predict the loss of performance in a kinetic condition, such as during a runner's heel strike through the roll off the toe. Typically, shoe manufacturers recommend discarding shoes every 400 miles. However, this varies depending on the number of compressions the shoe experiences during the recommended life. More specifically, the shoe manufacturers usually design their shoes to reach their end of life after approximately 400,000 compressions, which equates to 600 compressions per mile.

Shoe wear indicators are known in the art. For example, one reference discloses a wear indicator built into the shoe with a means to detect progressive loss of flexibility and cushioning of the shoe based upon the number of times it has been actuated and indicates this information to the user. In particular, the reference discloses a means to detect the actuation that is between the midsole and outersole of the shoe and uses a bladder. Changes in the bladder pressure are used to determine the shoes actuation.

Another example discloses a wear indicator for a shoe including an outsole and a midsole with wear indicators made of less compatible material vertically disposed within the midsole and a method to indicate the need to replace the shoe.

Another example discloses a shoe wear-out sensor that includes a detector for sensing a physical metric that wears out with the shoe, a processor, and an alarm for informing the user when the sole of the shoe is worn out. The detector is required to be a force sensing resistor or accelerometer and a processor configured to compare the acceleration against similar data of a new shoe. Additionally disclosed is a system including a detector, a processor which increments when the shoe is in use, and an alarm such as an LED or an audible device that is observable to the user during use.

Another example discloses a footwear having electronic circuitry associated with measuring usage comprising a power source, a first and second pressure switch which alternate between "on" and "off" and connected to a logic circuit with a decoder which sends information to a display mounted on the footwear.

Another example discloses a shoe wear indicator comprising an air bladder sensor unit, a microchip, a power supply/user interface and an interface cable housed within the insole. Further disclosed is a method of using the device in a combination of inserting the device into a shoe, using the shoe for physical activity, removing the device from the shoe, and downloading the usage data to the terminal.

Another example discloses a garment with a connected force sensor and a means of processing and analysing that sensor signal profile and then transmitting it to the wearer.

A disadvantage of the prior art is the placement of the device within the construction of the shoe, which requires that the design and manufacturing process of the shoe be altered. Furthermore, this requirement leads to the reduction in performance of the shoe both by the elimination of a portion of the cushioning foam and reduction in flexibility due to the addition of the device. For example, the placement of the device within the midsole or outsole requires the reengineering of the shoe to compensate for the loss of functionality, which would disallow the device from being incorporated in any existing shoe designs. Another example would be the incorporation of a less compactible material within the shoe which changes the supportive characteristics of the shoe design.

Another disadvantage of the prior art is the requirement of the sensor to be a combination of an air bladder and pressure sensor or a combination of an accelerator and force sensing resistor. The accuracy of these elements is affected by the environment around the sensor during use. For example, variations in atmospheric pressure or temperature may change the reference values needed to compare when the shoe is in use or not in use. In another example, the sensor is said to measure a physical metric that changes as the shoe wears out which requires that the sensor change correspondingly with the shoe. These disadvantages require a robust and complex analysis of the starting and ending state of the sensor throughout the shoe use and, in some cases, foreknowledge of the wear rate of the shoe.

Another disadvantage of the prior art is the inability to distinguish a non-destructive compression from a destructive compression. Although the art describes methods to make this comparison, such as the physical displacement of the sensor or the amount of acceleration above the minimal level, this analysis becomes more complicated as the shoe wears which will change the reference point, requiring a robust and complex analysis of the starting and ending state of the sensor. Other methods require foreknowledge of the user's weight, stance-to-foot swing phase and other values specific to the shoe construction.

Another disadvantage of the prior art is the requirement that the output of the information of the invention be transmitted outside the shoe or by removing the invention from the shoe and connected it to a terminal. In another art, the information is actively communicated to the user through a light or transmission while the device is in use. These elements may seem advantageous for some applications but the complexity of removing, analyzing the wear of the shoe, and reinserting the device back into the shoe greatly complicates both the use of the shoe and the interpretation of the use. This requirement increases user complexity and introduces the probability of errors and forgetfulness. For example, a blue wear indicator strip on the razor blade improved the user compliance better than other disassociated mnemonics. Furthermore, the communication of the device's information to the user during the device's use greatly complicates the designs, requiring that the indication means egress from the shoe or that the shoe be modified to allow egress in an unobtrusive way.

Yet another disadvantage of the prior art is the requirement that the device is constructed out of reusable materials which increases the cost of the device by the use of durable components that can be used again. Although this may be advantageous for some applications, the maintenance and reliability of such a reused device is an added burden to the user. For example, although the razor blade may be resharpened after it has reached its initial end of life, the complexity of sharpening it and the understanding of how many more sharpenings it should receive is more cumbersome than users are willing to tolerate and therefore they simply discard the used razor.

Accordingly, there is a need for a low cost device that measures the destructive compressions of the shoe in such a manner that it is self referencing and accumulates those compressions and can display the accumulation to the user within the shoe in a manner that is simpler for the user to interface with.

BRIEF SUMMARY OF THE INVENTION

The present invention tracks the accumulation of destructive compression cycles within a shoe and indicates the information to the user through a series of integrated indicators. The invention has an advantage of being able to be placed in any shoe without compromising the construction or performance of the shoe. An additional advantage of the invention is the improved accuracy of the information by improving both the stability and longevity of the sensor system and the ability to distinguish destructive, partially destructive and nondestructive compressions. Another advantage of the invention is the reduction of the cost of construction while achieving a lifetime in excess of the shoe. Yet another advantage of the invention is the user interface which is contained completely within the device allowing the user to view the information within the shoe.

The invention is further described by the method of its use with a shoe to measure the accumulating destructive compressions which include the steps of: (1) inserting the device into the shoe; (2) using the shoe in a destructive way; (3) the user activating the user interface; (4) the user deciding to continue to use the shoe or discontinuing use.

Although the invention described has a primary use of tracking the accumulation of destructive compressions to a shoe, other uses are imagined such as the accumulation of trauma to the users body when a shoe is not used, such as in natural, or barefoot, running.

BRIEF DESCRIPTION OF THE DRAWINGS

The elements of the invention can be more readily understood from the detailed description below with reference to the accompanying drawings herein.

DETAILED DESCRIPTION OF THE INVENTION

Figure 1:
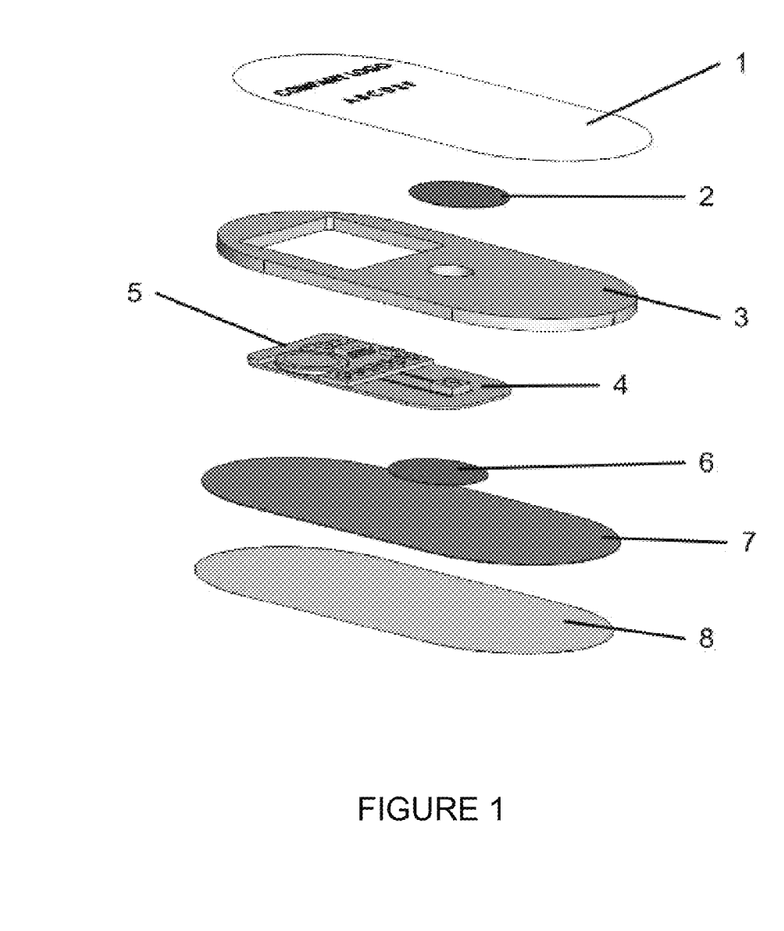
FIG. 1 is an exploded view of the device with an embodiment of the present invention.
Figure 2:
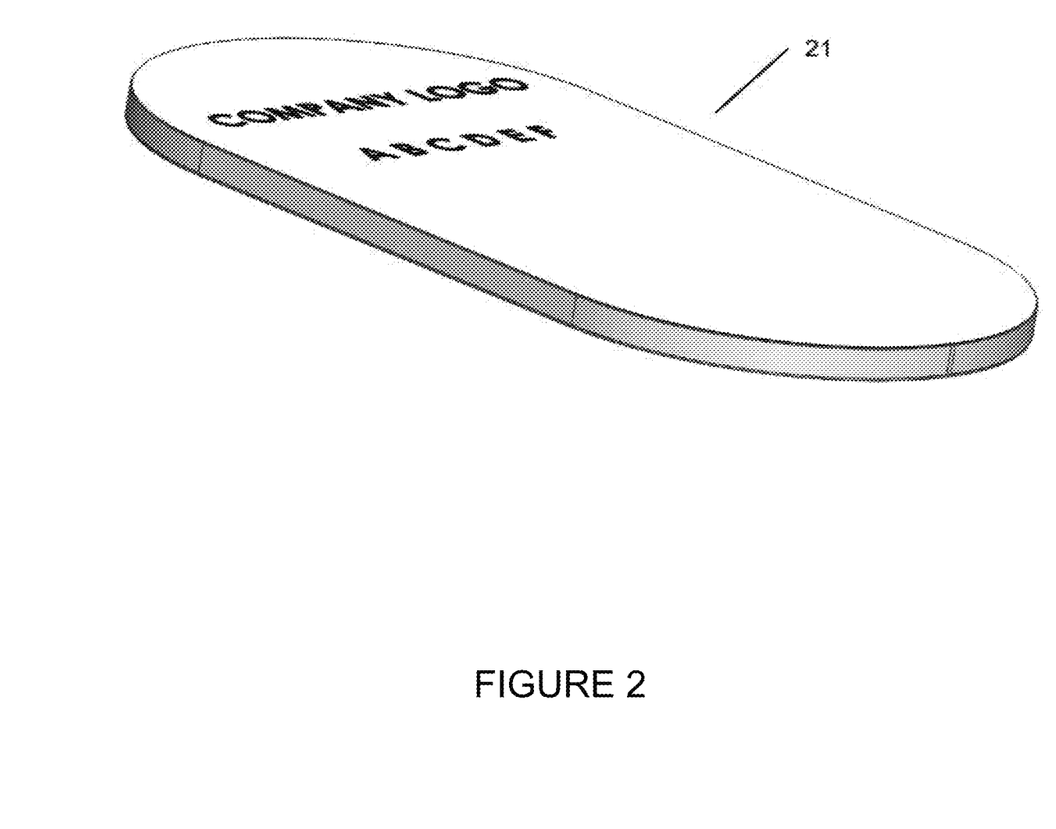
FIG. 2 is an isometric view of the inventive device.

As shown in FIG. 2, the inventive device 21 comprises an assembly of components, which are shown in the exploded view in FIG. 1. The device 21 comprises an assembly of the upper enclosing layer 1, the upper substantially rigid member 2, the microporous highly compressible foam member 3, the highly compressible area containing the electromechanical switch circuit 4, the highly incompressible area containing the electronic analysis components 5, the lower substantially rigid member 6, the flexible substrate 7, and the lower enclosing layer 8.

Figure 3:
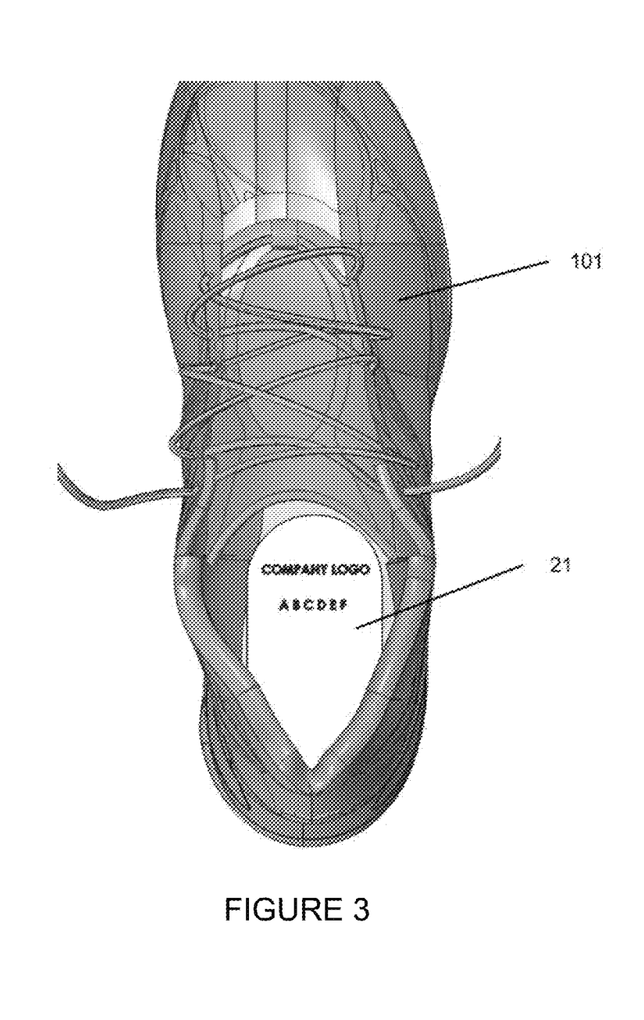
FIG. 3 is a top view in accordance with an embodiment of the present invention, which has been inserted into the shoe of a user.

In operation, the device 21 would be placed within the shoe under the sock liner, or insole, toward the heel and in contact with the upper side of the energy absorbing foam in the heel of the shoe, as shown in FIG. 3. The user would then engage in an activity, such as walking or running, which causes a force to be applied to the system, thereby causing partial failure of the energy absorbing foam. Although a single cycle of the force for the activity may not cause total failure to the energy absorbing foam, repeated compression cycles will accumulate enough partial failures to result in total failure to the energy absorbing foam. Additionally, the environment within the shoe may typically contain sweat and excess heat generated from the user during use. The environment may be naturally augmented by addition of water from rain or standing puddles that may enter the show during its use. The device 21 may be constructed of materials that inherently resist degradation throughout the life of the device, or separate the device from environment throughout its life. A method of using the device includes its insertion within the shoe, participating in an activity that compresses the device, physically interfacing with the device to determine its cumulative use, and the determination that the device has reached its end of useful life.

Figure 4:
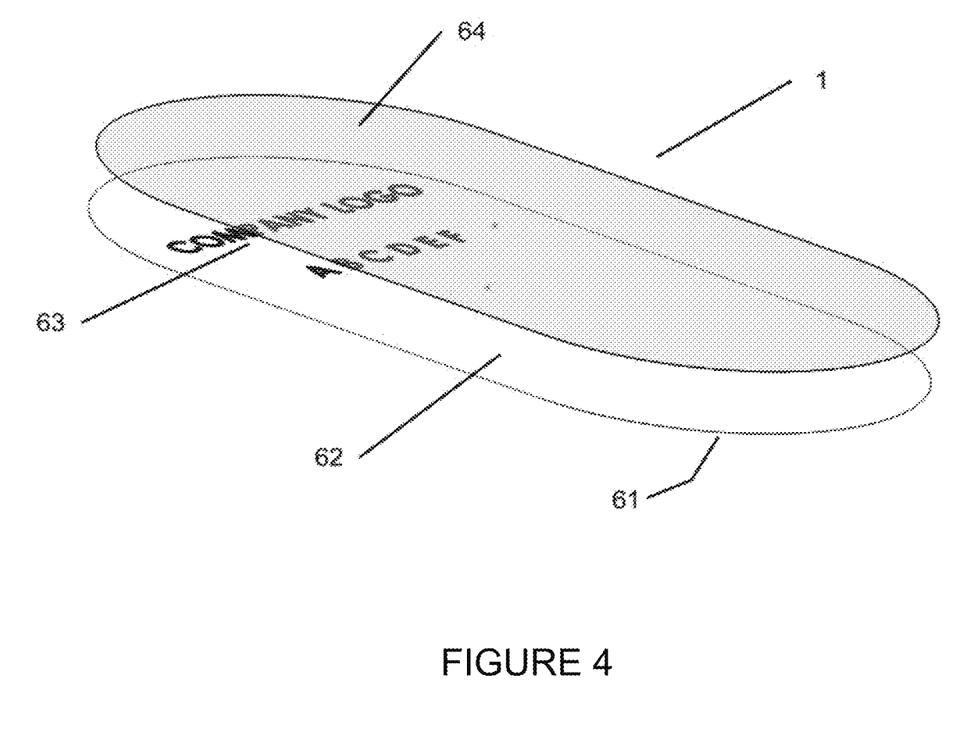
FIG. 4 is an illustration of one embodiment of the upper enclosing layer.

The upper enclosing layer 1, as shown in FIG. 4, may contain an adhesive layer 61 for attachment to the microporous highly compressible foam member 3 (see FIG. 1), a semitransparent continuous layer 62 to receive the artwork member 63, and a transparent continuous impermeable layer 64. The adhesive layer may be chosen from a variety of adhesives common to the fabrication of microporous foam devices. The preferred embodiment uses a pressure sensitive adhesive (PSA), such as 3M 300LSE, which increases its adhesive function throughout the compressive use of the device. The semitransparent continuous layer 62 functions to protect the inside of the device from exposure to the environment of the shoe and also serve to receive the artwork member 63. The materials of construction of the semitransparent continuous layer may be chosen from any material that is opaque under typical lighting to the user and will transmit light from the indicators. The preferred embodiment is constructed using a durable vinyl graphic film, such as 3M Controltac Plus Graphic Film, but other materials can be employed. The artwork member 63 may consist of the logos, instructions for use, and references to the wear reference values and is intended to convey information regarding the device 21 to the user. The materials of construction of the artwork member 63 may be chosen from any color-fast printing material and may be adhered to the semitransparent continuous layer through a variety of means including inkjet, silkscreen, or laser printing which are common to someone skilled in the art of printing. A preferred embodiment may be constructed with solvent based inks such that no deleterious effects occur to the artwork during the use of the device 21. For example, the high heat and moisture will not detrimentally affect a solvent based ink, thereby retaining the legibility of the artwork till the end of life of the invention. The transparent continuous impermeable layer 64 further protects the device from the environment found with the shoe. The materials of construction may be chosen from any lamination material typical to the lamination method, such as a film and adhesive material.

Figure 7:
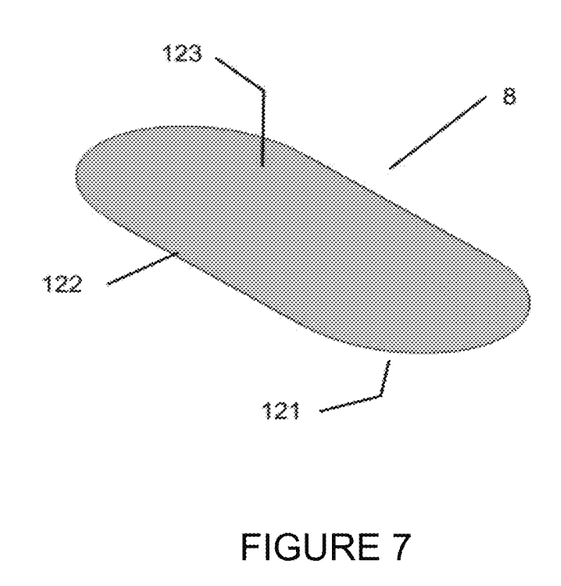
FIG. 7 is an illustration of one embodiment of the lower enclosing layer.

The lower enclosing layer 8, as shown in FIG. 7, contains a lower adhesive layer 121 for attachment to the shoe, a continuous impermeable layer 122, and an upper adhesive layer 123 for attachment to the flexible substrate 7 (see FIG. 1). The lower and upper adhesive layers 121, 123 may be chosen from a variety of adhesives common to the fabrication of microporous foam devices. A preferred embodiment uses pressure sensitive adhesive (PSA), such as 3M 300LSE, which increases its adhesive function throughout the compressive use of the device. The continuous impermeable layer 122 functions to protect the inside of the device from exposure to the environment of the shoe and assist the elements of the device to return to their original position after the compression cycle. The materials of construction may be chosen from any material with a high yield strength such that the flexing that occurs during the compression cycle is resisted and the layer is forced to return to its original position after the compression cycle. The materials of construction must also be chosen such that it resists moisture ingress. Although the layer may be constructed of materials such as spring steel or Polyimide film, one preferred embodiment uses polyester.

Figure 8:
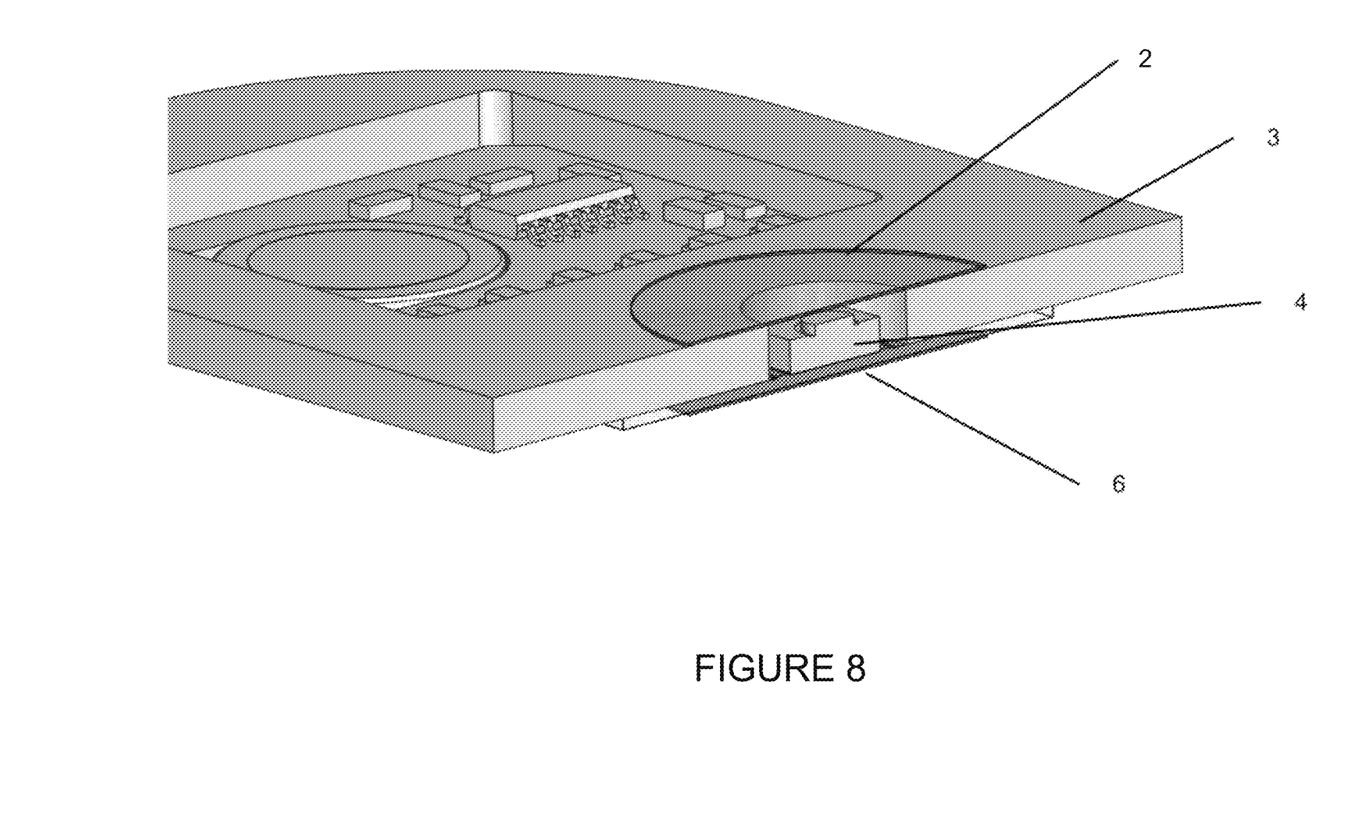
FIG. 8 is a cross sectional view of the highly compressible area.

The highly compressible area 5, shown in cross section in FIG. 8, functions to receive the compressive force from the heel of the user during the compression cycle, convert the compressive force to an electrical pulse and return the area to its original position after the compression cycle. The area contains the upper substantially rigid member 2, the microporous highly compressible foam member 3, the electromechanical switch 4, and the lower substantially rigid member 6. The upper substantially rigid member 2 functions to distribute the compressive force exerted by the heel of the user during the compression cycle to the electromechanical switch 4 and to the microporous highly compressible foam material 3. The material of construction of the upper and lower substantially rigid members 2, 6 are chosen such that, during a compression cycle, the material will resist deformation and not retain a permanent deformation and return to its original shape after the compression cycle. Although it can be constructed of any material that will not permanently deformed during the compression cycle, a material with a high yield strength is preferred, such as spring tempered stainless steel. The microporous highly compressible foam member 3 is chosen such that it compresses during the compression cycle and returns to its original shape after the compression cycle without retaining any permanent deformation or loss of height. Although any microporous material can be used, such as neoprene or silicone foam, a preferred embodiment uses a polyurethane high density foam, known as Poron. Particular to this invention is the choice of the microporous material with characteristics such that it generates a counter force greater than the nondestructive compressive force generated by the user. More particularly, the density and thickness of the microporous foam is chosen to overcome the compression force of the user such that the electromechanical switch 4 is not fully compressed. Also particular to this invention is the choice in the lateral width of the microporous foam member that is chosen to be significantly larger than the thickness of the foam member such that the compression cycle causes movement of the foam member predominantly perpendicular to the surface of the foam member. Although a variety of ratios could be established to achieve this objective, the preferred embodiment has a diameter of about two inches and a thickness about ⅛ of an inch.

Figure 9:
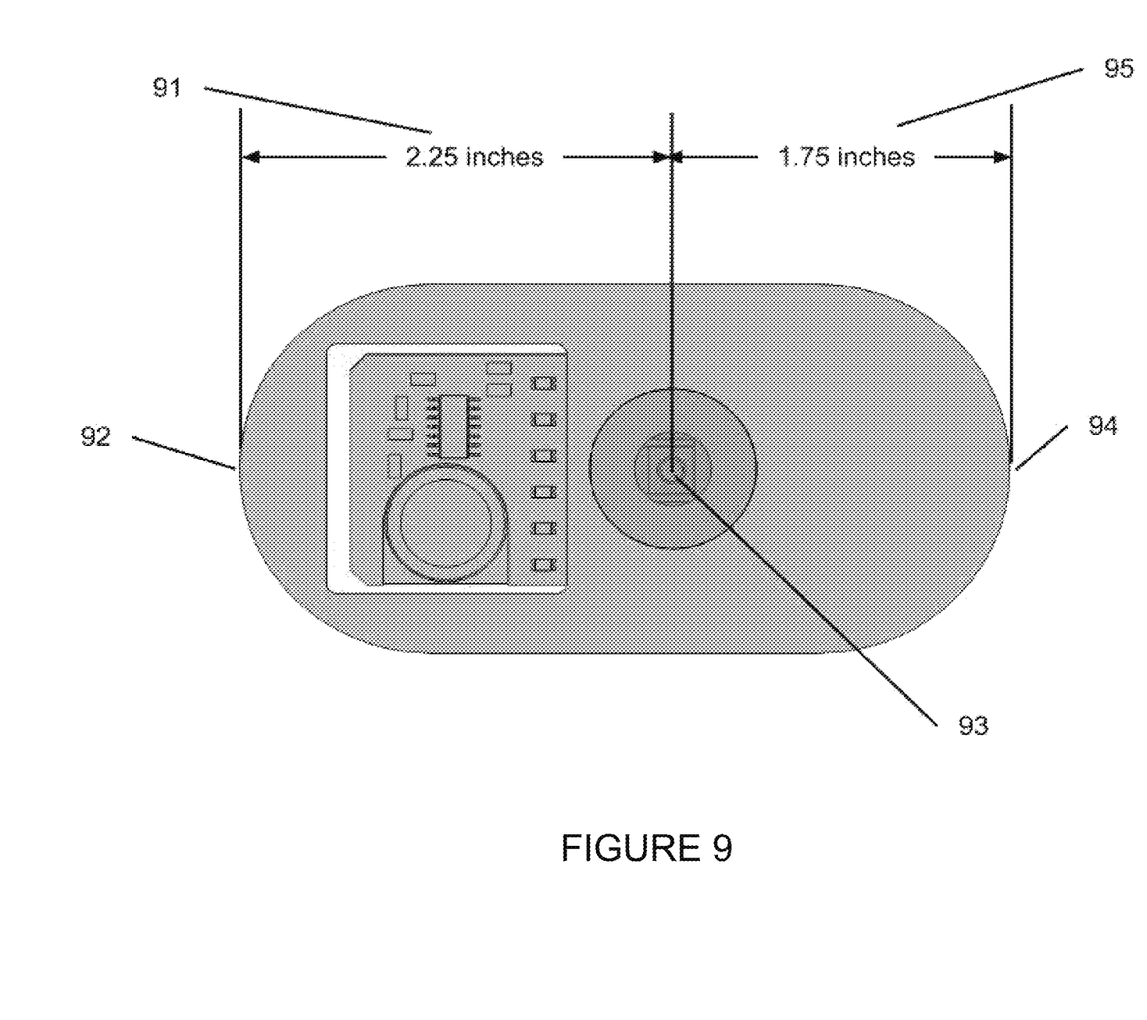
FIG. 9 shows the location of electromechanical switch in accordance with one embodiment.
Figure 10:
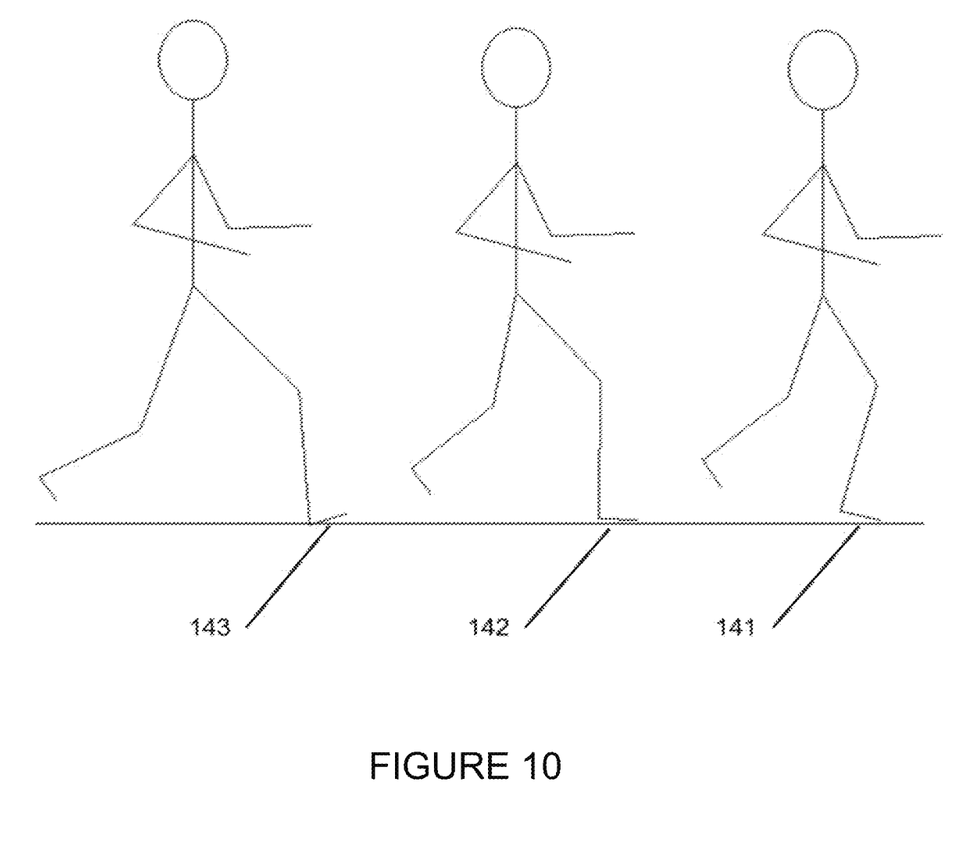
FIG. 10 is a pictorial representation of the angle between the ground and the shoe of the user.
Figure 11:
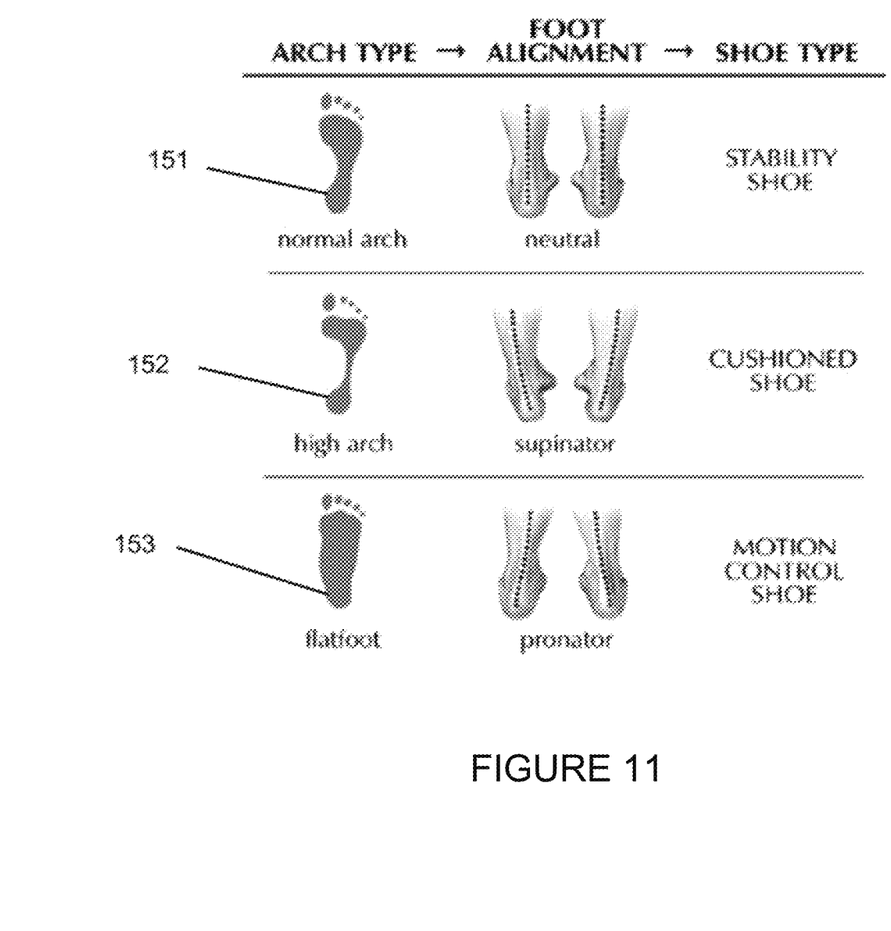
FIG. 11 is a set of typical footprints that represent the variety of users and the force imparted to the shoe of the user.

The electromechanical switch 4 is compressed during the compression cycle closing the electrical path connected to the electronics components in the highly incompressible area 5, thereby generating a corresponding electrical pulse. Although the materials of construction may be chosen from any that compress during the compression cycle and return to their original position after the compression cycle, the preferred embodiment uses a dome type switch which, when compressed, closes the electrical connection from the positive and negative side of the circuit. Dome type switches are known in the art and commonly found in electronic assemblies. Particular to this invention is the selection of a dome switch with an internal counter compression force, commonly referred to as activation force, that is great enough to resist the nondestructive compression force generated by the user during a compression cycle. Also particular to this invention is the location of electromechanical switch 4 relative to the end of one side of the invention as shown in FIG. 9. The location of the switch 4 is chosen to improve the accuracy of the invention such that the electromechanical switch 4 will be compressed, regardless of the angle between the ground and the shoe of the user shown in FIG. 10 or the distribution of the compression force based on the arch type, as shown in FIG. 11. A user with a high angle 143 (see FIG. 10) will transition from the heel to the toe during the activity, thereby compressing the electromechanical switch 4. However, if the location of the switch 4 were chosen to close to the heel a user with a low angle 142 or negative angle 141 may not overcome the internal counter compression force if the electromechanical switch 4 were located further back toward the heel. Also, if the arch of the user tends to be high 152 (see FIG. 11), the placement of the switch 4 toward the front of the arch will insure it is fully compressed during its use. The electromechanical switch 4 is centered between 1.5 and 2.0 inches from one end of the lower enclosing layer 8.

Figure 5:
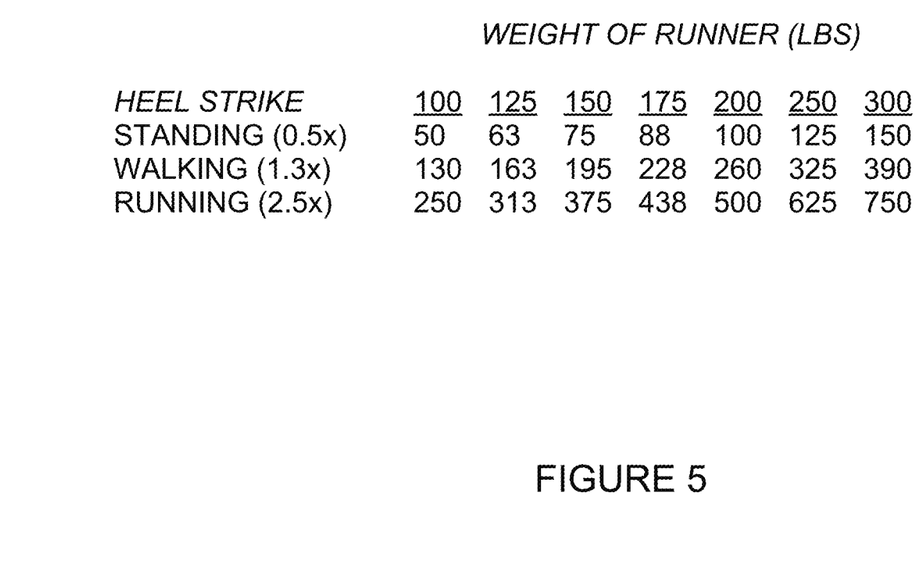
FIG. 5 is a table of the compression forces for a variety of users

The use of this device 21 may include activities that include fully destructive compressions and less destructive compressions, such as from walking. This can be better understood by FIG. 5, which shows the relative force of the heel strike for a variety of users as compared to their static standing weight. Thus, a distinction between a more destructive force and minimally destructive force can be created. Chockalingam, et. al. described in "A pilot study of the reaction forces at the heel during walking with the application of four different wound dressing" that the average force of a walking heel strike is 1.3 times the force of the user of the shoe. Therefore, it can be shown that a heel strike of, say 250 pounds, may produce a fully destructive compression of a shoe. Whereas, a 175 pound user, walking may produce a partially destructive compression. It is important to this device to be able to distinguish a partially destructive compression from a fully destructive compression.

Figure 12:
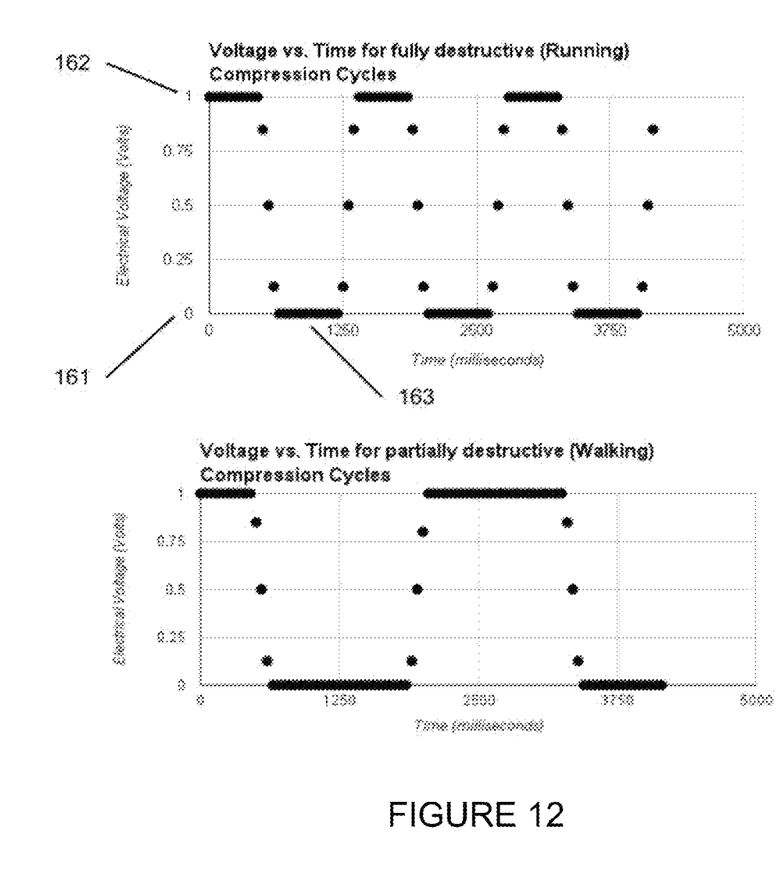
FIG. 12 is the time characteristic of the electrical pulse when different activities.

A single electrical pulse generated during the compression cycle by the electromechanical switch 4 corresponds to a single compression cycle. Particular to this invention is the pulse analysis method, which includes the comparison of the time characteristics of the pulse to predetermined reference values, and correspondingly augmenting the cumulative destructive value based on the result of this comparison. Critical to the accuracy of the cumulative destructive value is the determination of whether the compression cycle is non destructive, partially destructive, or fully destructive. A non-destructive compression cycle will not cause any actuation by the electromechanical switch 4, and therefore will not augment the cumulative destructive value. The determination of whether the compression cycle is partially or fully destructive is accomplished by the analysis of the time characteristics of the electrical pulse and by comparing the result of that analysis to predetermined reference values. The electrical pulse is described by the electrical voltage changing from one state to another as shown in FIG. 12. Although the electrical pulse can be arranged to change from a low voltage to a high voltage during the compression cycle, in one embodiment, the waveform changes from a high voltage 162 to a low voltage 161. The electrical pulse has a time characteristic which may be described by the length of time the electrical pulse remains in the low state 163. Specifically, the device distinguishes the types of compression cycles based on the length of time the electrical pulse is in the low state. The type of compression cycle is determined by comparing the length of time the pulse remains in the low state to a reference time period. The reference time period for the partially destructive cycle and fully destructive cycle are dependent on the internal counterforce of the highly compressible area 3 and may be determined empirically based on the specific design of the device 21. In one embodiment, it has been found that the reference time period for the fully destructive compression cycle is generally half the time of the partially destructive cycle. For example, the pulse will remain in the lower state for a longer time when the user is in a walking cycle because one foot of the user remains on the ground at all times. This distinction is used to augment the cumulative destructive value stored in the microcontroller.

Figure 13:
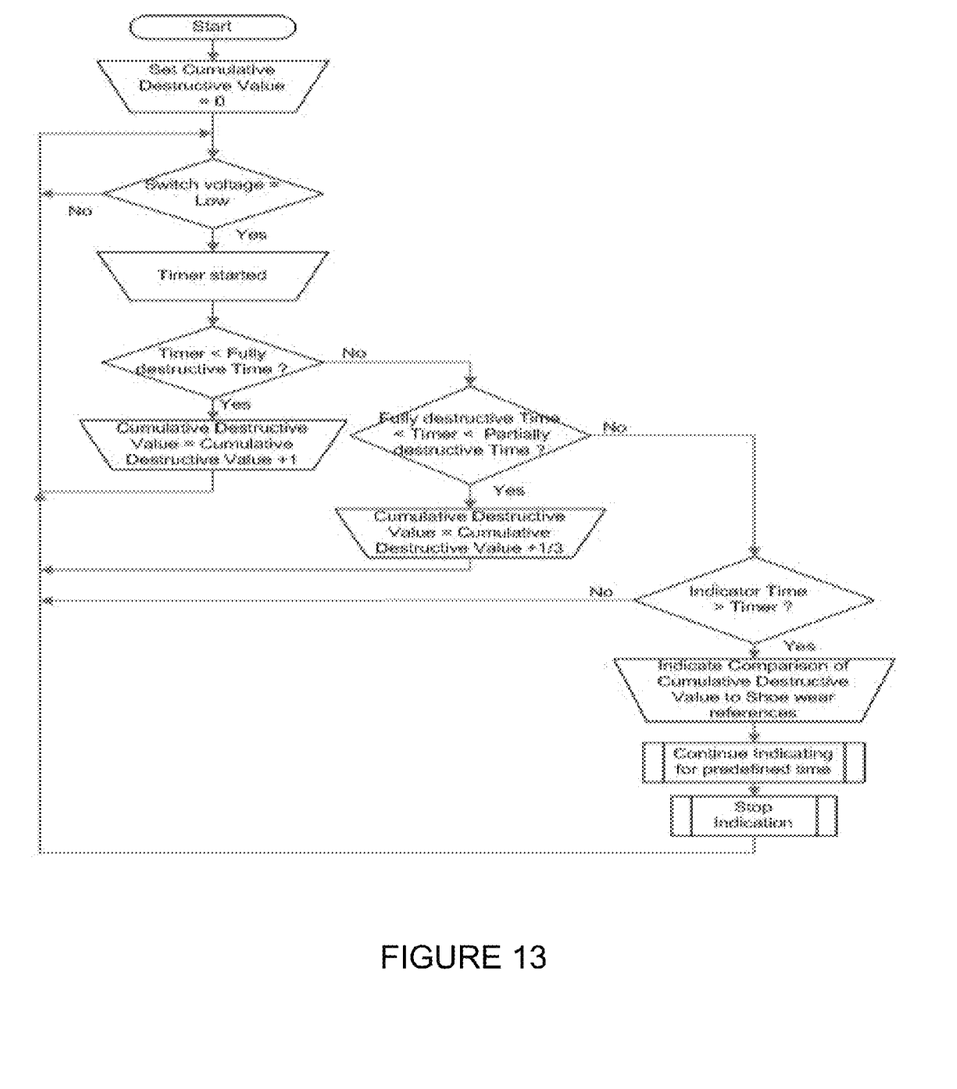
FIG. 13 is the flow chart of the software according to one embodiment.

The cumulative destructive value is used to summarize the total use of the device 21 within the shoe and is correlated to the total wear of the shoe by the user. The value is stored in the memory of the microcontroller and is augmented by the logic of the internal software shown in FIG. 13. The electronics of the device 21 include a microcontroller, or any suitable processing unit. That processing unit is in electrical communication with a storage device, such as a memory. The memory may be static or dynamic. Furthermore, it may be volatile or non-volatile. In some embodiments, a non-volatile memory is used to store the instructions executed by the processing unit. The non-volatile memory, such as EEPROM or FLASH ROM, may be a separate component, or may be embedded in the processing unit. The electronics may include RAM to hold dynamic data, such as counters and other variables. Further, the electronics may include indicating means that allow the results from the device 21 to be viewed by the user.

Returning to FIG. 13, the cumulative destructive value is set to zero at the beginning of the use of the device 21 and is augmented in value throughout the use of the device. The pulse analysis method also includes the augmentation of the cumulative destructive value by an amount corresponding to a partially destructive or fully destructive compression. Specifically, the cumulative wear counter will be augmented by a smaller amount, such as of a unit, for a partially destructive compression cycle and a full unit for a fully destructive compression cycle. The cumulative destructive value is used by the comparative indication method to indicate the cumulative wear of the device. The augmentation determines the cumulative destruction of the shoe. This value is then used to create an indication to the user.

The comparative indication method includes comparing the cumulative destructive value to predetermined shoe wear references and indicating the cumulative destructive value to the user, such as by an integrated visual display. The predetermined shoe wear references may be established by the manufacturers of the shoes. For example, typically, a running shoe manufacturer will recommend the shoe be replaced at about 400 miles, or about 250,000 compression cycles. Although the shoe wear reference may be chosen to be exactly the same as the recommended value, a lower or higher value may be chosen to accommodate the type of shoe in which the invention is used. In one embodiment, the indication may comprise a visual display assembly that may include a plurality of illuminating elements that are electrically connected to the microcontroller. The comparative indication method includes comparing the cumulative destructive value to various percentages of the show wear reference number and providing an indication to the user. For example, in one embodiment, if the cumulative destructive value is greater than about of $\frac{1}{3}$ the shoe wear reference number, a first indicator may be illuminated. If the cumulative destructive value is greater than a second percentage of the show wear reference number, such as about $\frac{3}{4}$ of the shoe wear reference number, a second indicator may be illuminated. If the cumulative destructive value is greater than a third percentage, such as about $\frac{7}{8}$ of the shoe wear reference, a third indicator may be illuminated. If the cumulative destructive value is about equal to the shoe wear reference number, a fourth indicator may be illuminated. Other percentages may be used, and different numbers of indicators may also be employed. The indicators are located within the highly incompressible area 5 and are electrically illuminated by the microprocessor. Although the indicators can be comprised of any type of electrical light, a preferred embodiment may use surface mount LEDs. The choice of the four indicators is chosen such that a user would be given sufficient warning to the user that the shoe should be replaced before they enter into a training routine or race. Additionally, more indicators can be used to indicate other functions. For example, the indicators can be chosen to occupy the same general space but be composed of different colorations or the indicator can be a single LED which changes colors through the variation of applied voltage. Additionally, an indicator can be used to demonstrate that the device is working correctly or another indicator can be used to demonstrate that the invention is augmenting the cumulative destructive value correctly. Once illuminated, the visual display may remain illuminated for a fixed period of time, or may be controlled by a user operation, such as actuation of a button or switch.

Figure 6:
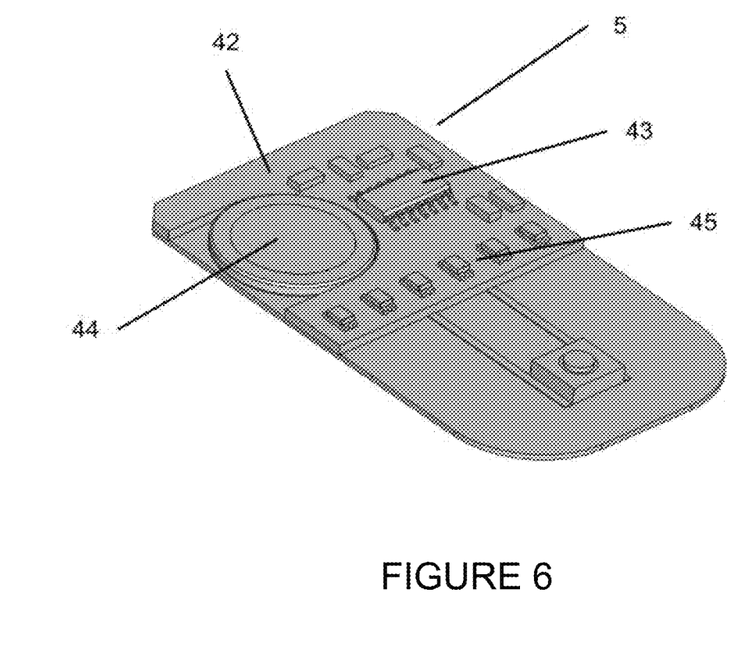
FIG. 6 is a view of the highly incompressible area.

The highly incompressible area 5 shown in FIG. 6 contains a substantially inflexible circuit board 42, an electronic microcontroller 43 to receive the electronic pulse from the electromechanical switch 4, a power supply 44, a highly incompressible impermeable coating (not shown for clarity) and a visual display assembly 45. The highly incompressible area functions to receive the electrical pulse from the electromechanical switch 4 and analyze its characteristics and display an indication of the cumulative destructive value visually to the user. The substantially inflexible circuit is constructed of materials common to the methods of PCB construction and is chosen of a thickness that is substantially inflexible during the compression cycle. The power supply is an electrical power supply chosen appropriately to power the microprocessor and the visual display assembly. In one preferred embodiment, the power supply is a lithium coin battery, however a plurality of power supplies may be used. For example, two or more power sources may be used to separately energize the visual display assembly and the electronic microcontroller. The electronic microcontroller executes the incorporated software of FIG. 13 to receive the input of the electrical pulse from the electromechanical switch 4, analyze its characteristics, accumulate a wear value, and energize the visual display assembly. Although any electronic microcontroller can be chosen, in one embodiment, an Atmel ATINY microcontroller is used. The highly incompressible impermeable coating functions to isolate the electronic components from the environment of the shoe and mechanically stabilize the electronic components from the flexing forces of the compression cycle. Although any coating typical for the encapsulation of electronics can be chosen, a preferred coating may be Loctite E-05cl epoxy. It should be noted that in accordance with one embodiment, this device is manufactured using a cast-in-place assembly method. Although cast-in-place, or molding methods, are known in the art for electronics encapsulation, the choice of a sufficiently dense microporous foam material and a conformal coating with a rapid curing rate and sufficiently high viscosity such that the conformal coating may be injected into the open area above the electronic components thereby filling the open areas and the conformal coating curing before it penetrates into the microporous foam thereby degrading the performance of the microporous foam is specific to one embodiment.

The flexible electrical substrate 7 (see FIG. 1) functions to stabilize the device, retain the elements in their arrangement, and retain the electrical interconnections between the electrical components of the highly compressible area 4 and the electrical components of the highly incompressible area 5. The material of construction is chosen with a sufficient tensile yield strength to return to the original shape after the compression cycle such as fiberglass resin, polyimide, or polyester PCBs or a lamination of spring tempered steel alloy and an insulative layer. The electrical interconnections are constructed of materials typical for PCB fabrication, such as copper traces.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A device for indicating shoe wear for use with a running shoe, comprising:

a flexible electrical substrate with two electrically interconnected areas, a first of the electrically interconnected areas that is highly compressible and a second electrically interconnected area;
a upper enclosing layer; and
a lower enclosing layer;
wherein the first highly compressible area is compressible predominantly in a direction perpendicular to its surface and comprises an electromechanical switch to convert a compression of the highly compressible area, caused from use of the device, into an electrical pulse and wherein the highly compressible area returns to its original shape between compressive uses; and
wherein the second area receives the electrical pulse from the first area and comprises:
a processing unit executing a pulse analysis method to analyze characteristics of the electrical pulse and augment a cumulative destructive value accordingly, and executing a comparative indication method which compares the cumulative destructive value to a shoe wear reference value and determines an indication of the shoe wear, and
a visual indicator to display the indication of shoe wear.

2. The device of claim 1, wherein the generation of an electrical pulse is produced by the actuation of the electromechanical switch during the compression of the highly compressible area, wherein the pulse comprises a high voltage state for a first time period and at a low voltage state for a second time period, where the two time periods are related to the density of material used in the highly compressible area and closure force of the electromechanical switch.

3. The device of claim 1, wherein the highly compressible area is centered between 1.5 and 2.0 inches from one end of the bottom enclosing layer.

4. The device of claim 1, where the pulse analysis method comprises:
comparing the time an electrical pulse is at a low voltage state to a partially destructive value and incrementing the cumulative destructive value by a portion of a unit;
comparing the time the electrical pulse is at a low voltage state to a fully destructive value and incrementing the cumulative destructive value by a full unit; and
comparing the time the electrical pulse is at a low voltage state to a walk time value and not incrementing the cumulative destructive value.

5. The device of claim 1, wherein the comparative indication method comprises:
comparing the cumulative destructive value to a first percentage of the shoe wear reference number and illuminating a corresponding indicator,
comparing the cumulative destructive value to a second percentage of the shoe wear reference number and illuminating a corresponding indicator,
comparing the cumulative destructive value to a third percentage of the shoe wear reference and illuminating a corresponding indicator,
and comparing the cumulative destructive value to the shoe wear reference number and illuminating a corresponding indicator.

6. The device of claim 4, wherein the first percentage is ⅓, the second percentage is ¾, and the third percentage is ⅞.

7. The device of claim 1, wherein the visual indicator comprises a plurality of lights electrically connected to the processing unit.

8. The device of claim 1, wherein the flexible electrical substrate comprises a material with sufficient tensile yield strength to return to the original shape after a compressive use, and comprises electrical pathways to electrically connect the two areas.

9. The device of claim 8, wherein said flexible substrate comprises fiberglass resin, polyimide, or polyester PCBs or a lamination of spring tempered steel alloy and an insulative layer.

10. The device of claim 1, wherein the top enclosing layer comprises a lamination comprising an adhesive for attachment to the flexible electrical substrate, a semitransparent continuous layer, an artwork member and a transparent continuous impermeable layer.

11. The device of claim 10, wherein the artwork member comprises a logo and a series of shoe wear reference annotations corresponding to the visual indicator.

12. The device of claim 1, wherein the bottom enclosing layer comprises a lamination comprising a lower adhesive for attachment to the running shoe, a continuous impermeable layer with a high yield strength such that it returns to its original shape after a compressive use, and an upper adhesive for attachment to the flexible electrical substrate.

13. The device of claim 1, wherein the first highly compressible area further comprises a lower substantially rigid member, a microporous highly compressible foam material, and an upper substantially rigid member.

14. The device of claim 1, wherein the second area further comprises a substantially inflexible circuit board, a power supply, and a highly incompressible impermeable coating.

* * * * *